(12) United States Patent
Van Meel et al.

(10) Patent No.: US 10,816,617 B2
(45) Date of Patent: Oct. 27, 2020

(54) METHOD AND SAFETY MODULE FOR AN AUTOMATIC OR SEMI-AUTOMATIC DETECTION WHETHER AN MR EXAMINATION OF A PERSON IS APPROVED WITH A PREDETERMINED MR SYSTEM

(71) Applicant: KONINKLIJKE PHILIPS N.V., Eindhoven (NL)

(72) Inventors: Marius Johannes Van Meel, Eindhoven (NL); Paul Augustinus Peter Kaufholz, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 460 days.

(21) Appl. No.: 15/554,101

(22) PCT Filed: Feb. 25, 2016

(86) PCT No.: PCT/EP2016/053896
§ 371 (c)(1),
(2) Date: Aug. 28, 2017

(87) PCT Pub. No.: WO2016/142174
PCT Pub. Date: Sep. 15, 2016

(65) Prior Publication Data
US 2018/0038923 A1 Feb. 8, 2018

Related U.S. Application Data

(60) Provisional application No. 62/160,715, filed on May 13, 2015.

(30) Foreign Application Priority Data

Mar. 9, 2015 (EP) ..................................... 15158186

(51) Int. Cl.
*G01R 33/28* (2006.01)
*A61B 5/055* (2006.01)
(Continued)

(52) U.S. Cl.
CPC ............ *G01R 33/288* (2013.01); *A61B 5/055* (2013.01); *A61B 5/4343* (2013.01);
(Continued)

(58) Field of Classification Search
CPC .. G01R 33/288; G01R 33/546; G01R 33/543; A61B 5/4887; A61B 5/4343; A61B 5/055; A61B 2560/0266
See application file for complete search history.

(56) References Cited

U.S. PATENT DOCUMENTS 7,259,560 B2 8/2007 Yamanaka
2002/0077537 A1* 6/2002 Avrin ................. A61B 5/04005
600/409

(Continued)

FOREIGN PATENT DOCUMENTS

| JP | 2011183072 A | 9/2011 |
| JP | 2013063148 A | 4/2013 |
| WO | 2014129426 A1 | 8/2014 |

OTHER PUBLICATIONS

V0n Smekal A. et al: "Evaluation and prediction of the influence of time varying gradient fields during MR-examinations on implanted cardiac pacemaker systems",Pr0ceedings 0f the Internati0nal S0ciety f0r Magnetic Res0nance in Medicine, vol. 2, Aug. 6, 1994 (Aug. 6, 1994), p. 1076.

(Continued)

*Primary Examiner* — Sanjay Cattungal

(57) ABSTRACT

A method for an automatic or semi-automatic detection whether an MR examination of a person (12) is approved with a predetermined MR system (10) includes the following steps:

(Continued)

Step 1: providing information whether and which contra-indication for such an MR examination is present for this person (12) (S1);
Step 2: providing information about a location of a cause (30) of the contra-indication within the person (12) (S2);
Step 3: determining a position of this cause (30) during the MR examination of the person with respect to at least one magnetic field coil (14, 16, 18) (S3);
Step 4: determining at least one characteristic parameter of the magnetic field generated by the coil (14, 16, 18) at the position of the cause (30) during the MR examination (S4); and
Step 5: automatically checking whether the MR examination is approved for the combination of the determined cause (30) of the contra-indication and the determined characteristic parameter of the magnetic field at the location of the cause (30) (S5).

19 Claims, 6 Drawing Sheets

(51) Int. Cl.
*A61B 5/00* (2006.01)
*G01R 33/54* (2006.01)
(52) U.S. Cl.
CPC ......... *A61B 5/4887* (2013.01); *G01R 33/546* (2013.01); *A61B 2560/0266* (2013.01); *G01R 33/543* (2013.01)

(56) References Cited

U.S. PATENT DOCUMENTS

| | | | | |
|---|---|---|---|---|
| 2003/0083588 | A1* | 5/2003 | McClure | A61B 5/05 600/547 |
| 2003/0216632 | A1* | 11/2003 | McClure | A61B 5/05 600/409 |
| 2004/0135687 | A1* | 7/2004 | Keene | G01V 11/00 340/551 |
| 2004/0147833 | A1 | 7/2004 | Czipott et al. | |
| 2006/0167496 | A1 | 7/2006 | Nelson et al. | |
| 2008/0242944 | A1* | 10/2008 | Sharma | A61B 5/411 600/300 |
| 2010/0121179 | A1* | 5/2010 | Min | G01R 33/583 600/421 |
| 2010/0179763 | A1 | 7/2010 | Overall et al. | |
| 2010/0312091 | A1* | 12/2010 | Krueger | G01R 33/285 600/410 |
| 2011/0092799 | A1 | 4/2011 | Steckner | |
| 2012/0086449 | A1* | 4/2012 | Graesslin | G01R 33/285 324/309 |
| 2012/0112747 | A1 | 5/2012 | Alexiuk et al. | |
| 2012/0245452 | A1* | 9/2012 | Doerr | A61N 1/3718 600/411 |
| 2012/0253426 | A1* | 10/2012 | Ellingson | A61N 1/3718 607/63 |
| 2013/0116750 | A1 | 5/2013 | Schmidt et al. | |
| 2014/0257089 | A1* | 9/2014 | Rapoport | G01R 33/288 600/424 |
| 2015/0212179 | A1 | 7/2015 | Overall et al. | |

OTHER PUBLICATIONS

Graesslin I et al: "Continuous Monitoring of RF-safety for Implantable MR-conditional Devices", InternatiOnal SOciety fOr Magnetic ResOnance in Medicine. Scientific Meeting and ExhibitiOn. PrOceedings, InternatiOnal SOciety Fdr Magnetic ResOnance in Medicine, US, vol. 17, Apr. 18, 2009 (Apr. 18, 2009), p. 4793.

Krueger S et al: "Permanent Non-invasive Device Safety Monitoring for Clinical MRI", InternatiOnal Society for Magnetic Resonance in Medicine. Scientific Meeting and Exhibition. Proceedings, International Society for Magnetic Resonance in Medicine, US, vol. 16, Apr. 19, 2008 (Apr. 19, 2008), p. 896.

Schaefers G: "Testing MR Safety and Compatibility",IEEE Engineering in Medicine and Biology Magazine, IEEE Service Center, Pisacataway, NJ, US,vol. 27, No. 3, May 1, 2008 (May 1, 2008), pp. 23-27.

Van Den Bergen B et al: "The effect of body size and shape on RF safety and BI field homogeneity at 3T", International Society for Magnetic Resonance in Medicine. Scientific Meeting and Exhibition. Proceedings, International Society for Magnetic Resonance in Medicine, US, No. 14, Apr. 22, 2006 (Apr. 22, 2006), p. 2040.

A.M. Sawyer-Glover et al "Pre-MRI Procedure Screening: Recomendations and Safety Considerations for Biomedical Implants and Devices" Journal of Magnetic Resonance Imaging, 12, p. 92-106 (2000).

* cited by examiner

METHOD AND SAFETY MODULE FOR AN AUTOMATIC OR SEMI-AUTOMATIC DETECTION WHETHER AN MR EXAMINATION OF A PERSON IS APPROVED WITH A PREDETERMINED MR SYSTEM

CROSS REFERENCE TO RELATED APPLICATIONS

This application is a U.S. national phase application of International Application No. PCT/EP2016/053896, filed on Feb. 25, 2016, which claims the benefit of U.S. provisional Application Ser. No. 62/160,715 filed on May 13, 2015 and EP Application Serial No. 15158186.5 filed Mar. 9, 2015 and is incorporated herein by reference.

FIELD OF THE INVENTION

The invention relates to a method for an automatic or semi-automatic detection whether an MR examination (MR: Magnetic Resonance) of a person is approved with a predetermined MR system, which system includes at least one coil for generating a magnetic field. The invention further relates to a corresponding safety module for an automatic or semi-automatic detection whether an MR examination of a person is approved with a predetermined MR system, which system includes at least one coil for generating a magnetic field and the invention relates to a corresponding MR system.

BACKGROUND OF THE INVENTION

Persons to be examined by use of a MR system, in general patients, may have implanted medical devices. In general these are contra-indicated for MR unless they are tested 'MR conditional'. In that case it is possible to perform an MR examination if these conditions of use are strictly adhered to.

It is difficult to enter information of implant MR conditions into conventional MR systems. Often indirect parameter controls need to be applied assuming a lot of technical knowledge of the MR operator or MR user. This complexity leads to user errors with patient harm as a potential result.

The US patent application US2010/0312091 is concerned with the problem of excessive heating during radio frequency excitation due an interventional instrument or an implant.

SUMMARY OF THE INVENTION

It is an object of the invention to provide a method, a safety module and an MR system for an automatic or semi-automatic detection whether an MR examination of a person is approved with a predetermined MR system, which enable a safe MR examination.

According to various embodiments of the invention, the method comprises the following steps:
(i) providing information whether and which contra-indication for such an MR examination is present for the person to be examined;
(ii) providing information about a location of a cause of the contra-indication within the person;
(iii) a determination of a position of this cause during the MR examination of said person with respect to the coil;
(iv) a determination of at least one characteristic parameter of the magnetic field generated by said coil at said position of the cause during the MR examination; and
(v) an automatic check, whether the MR examination is approved for the combination of the determined cause of the contra-indication and the determined characteristic parameter of the magnetic field at the position of said cause.

This method structures and automates the detection whether an MR examination (MR: Magnetic Resonance) of a person is approved with a predetermined MR system, and therefore reduces the risk of user errors. In this context an approved MR examination of a person with a predetermined MR system is an examination which is safe/not dangerous for this individual person. The determination in step (iv) preferably is an automatic determination. Information on whether a contra-indication applies for the patient to be examined may be automatically accessed from a radiology-information-system (RIS) in which information and status of the patient already has been entered prior to the execution of the present invention. The information of the location of the cause of the contra-indication, e.g. the location of the implant, may also be accessed automatically from the RIS. Further, the determination of the characteristic parameter of the magnetic field at the location of the cause of the contra-indication may be automatically derived from a selected examination protocol, e.g. implemented as an Examcard. From the selected examination protocol, the acquisition pulse sequences and their gradient waveforms and radio frequency (RF) pulse characteristics are derived. The characteristic parameters of the magnetic field may be the strength of the main magnetic field, the gradient strengths of the gradient fields and the RF (B1) fields of the acquisition sequences of the selected examination protocol. The examination protocol may be selected in advance and available from the RIS. The acquisition pulse sequences entail gradient strengths, gradient slew rates and RF pulse shapes and strengths. These determined one or more characteristics of the magnetic field(s) form input for the automatic check in which the (selected) MR examination is assessed for approval to be executed with the patient to be examined for which a contra-indication applies. Notably, the contra-indication may be related to an MR-conditional status of an implant and the assessment aims at a verification that the applicable constraints will be meet if the MR examination is executed.

According to a preferred embodiment of the invention, one or both of the information providing steps (i) and (ii) is/are performed by use of a manual input and/or a manual selection from a list presented by a user interface (UI). Instead of providing information about the location of the cause of the contra-indication within the person, information about the position of this cause during the MR examination of said person with respect to the coil can be provided directly by use of the user interface. The UI simplifies the input and directly controls the relevant MR parameters to stay within the implant conditions, thereby further reducing the risk of user errors.

The above complexity also means some institutes will be hesitant to use the superior diagnostic qualities of MR on persons with implants to reduce risk. The user interface UI will facilitate these institutes to scan persons they would normally have sent away. Preferably, the information about potential contra-indications for an MR examination of the person is requested/interrogated by a request routine/interrogation routine, which is performed automatically on the user interface.

According to another preferred embodiment of the invention, the method further comprising a following step (vi) of an automatic release of the MR examination of the person in case the MR examination is approved and an automatic blocking of the MR examination of the person in case the MR examination is not approved.

According to yet another preferred embodiment of the invention the identity of the person is specified before determining the contra-indication in step (i). Thus, step (i) is a step of specifying the identity of the person and providing information whether and which contra-indication for such an MR examination is present for this person.

According to another preferred embodiment of the invention, the characteristic parameter of the magnetic field generated by the at least one coil is a field gradient.

According to yet another preferred embodiment of the invention the cause of the contra-indication is an implant (an implanted medical device) or a pregnancy of the person.

The invention further relates to a computer program product for executing the aforementioned method.

According to various embodiments of the invention, the safety module for an MR system has access to the technical characteristics of the MR system and is configured to perform:

a receipt of information (a) about a position of a cause of the contra-indication during the MR examination of said person with respect to the at least one coil; and/or (b) about a location of the cause of the contra-indication within the person followed by an automatic determination of a position of this cause during the MR examination of said person with respect to the at least one coil;

a determination, especially an automatic determination, of at least one characteristic parameter of the magnetic field generated by said coil at said position of the cause during the MR examination; and an automatic check, whether the MR examination is approved for the combination of the determined cause of the contra-indication and the determined characteristic parameter of the magnetic field at the position of said cause.

According to a preferred embodiment of the invention one or more of the first two steps is/are performed by use of a manual input and/or a manual selection from a list presented by a user interface of an input terminal. Preferably, the information about potential contra-indications for an MR examination of the person is interrogated by a request routine, which is performed automatically on the user interface.

According to another preferred embodiment of the invention the module is further established to send a control signal to a control unit of the MR system to perform an automatic release of the MR examination of the person in case the MR examination is approved and an automatic blocking of the MR examination of the person in case the MR examination is not approved.

According to yet another preferred embodiment of the invention the characteristic parameter of the magnetic field generated by the at least one coil is a field gradient.

According to various embodiments of the invention, the MR system includes a control unit, at least one coil for generating a magnetic field and the aforementioned safety module. The MR system is, for example, an MR system with an MRI scanner, which scanner comprises the control unit and the coils.

According to a further embodiment of the invention, the MR system comprises:

a gradient system to apply a gradient magnetic field in an examination zone, in which the safety module includes a user interface, and the safety module being configured to display the gradient strength distribution on the user interface, in particular to highlight regions in which the gradient strength exceeds a pre-set safety level. This display of the gradient field strength enables the operator to avoid that interventional instruments of implants (in the patient to be examined) reach regions where the gradient strength is dangerously high. This is facilitated in an easy manner to pre-set the maximum safety level of the gradient strength, in particular in dependence of the implant or interventional instrument that is expected to be entered into the examination zone. Then, preferably, the regions of the gradient strength where the pre-set maximum level is exceeded are highlighted on the user interface. The gradient strength distribution may be displayed for the volume in which the gradient magnetic fields are applied within the magnetic resonance examination system as well as regions outside of the magnetic resonance examination system that the patient to be examined is moved through when positioned in magnetic resonance examination system's examination zone

BRIEF DESCRIPTION OF THE DRAWINGS

These and other aspects of the invention will be apparent from and elucidated with reference to the embodiments described hereinafter.

In the drawings:

FIG. 4 shows a second request-mask of the request routine;

FIG. 5 shows a third request-mask of the request routine;

FIG. 6 shows a fourth request-mask of the request routine; and

DETAILED DESCRIPTION OF EMBODIMENTS

Figure 1:
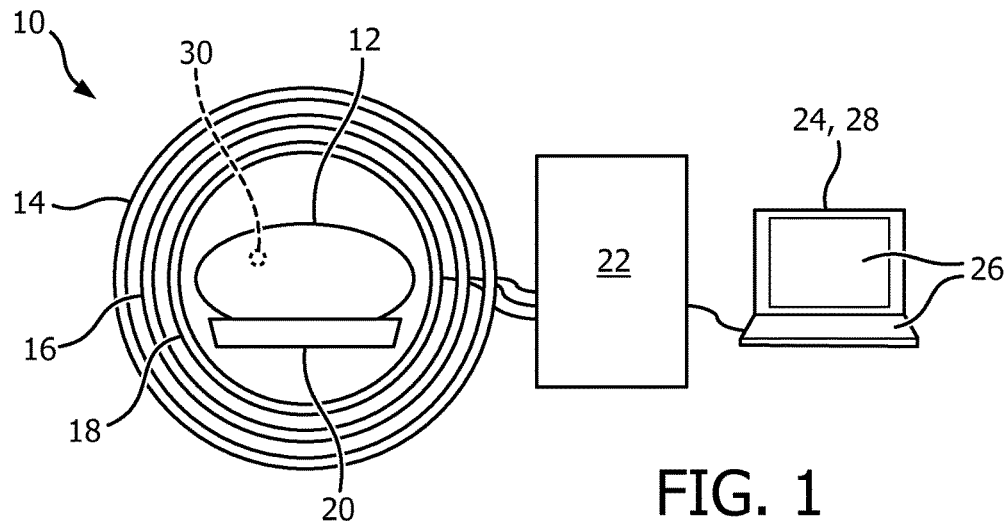
FIG. 1 shows a schematic representation of a MR system including a safety module.

FIG. 1 shows a schematic representation of a MR system 10 for performing an MR (MR: Magnetic Resonance) examination of a person (in general a patient) 12, the system 10 comprises a plurality of coils 14, 16, 18 including a field coil 14, a gradient field coil 16 and an RF coil 18 (RF: Radio Frequency), a patient bed 20, a corresponding control unit 22 for controlling the MR examination, a personal computer 24 with a processor (not shown), a memory (not shown) and at least one user interface 26 (including the necessary hardware: display, keyboard, mouse, etc.). A safety module 28 of said MR system 10 is made up of said computer 24. The person 12 to be MR examined has got an unsafe implant, which is a cause 30 of a contra-indication for such an MR examination.

In the following discussion reference is made to a method for a semi-automatic detection whether an MR examination of a person is approved with a predetermined MR system 10, which method is performed by use of the user interface (UI) 26. The invention is however applicable with other devices for providing adequate information either. The use of the UI 26 is selected as a preferred example.

Figure 2:
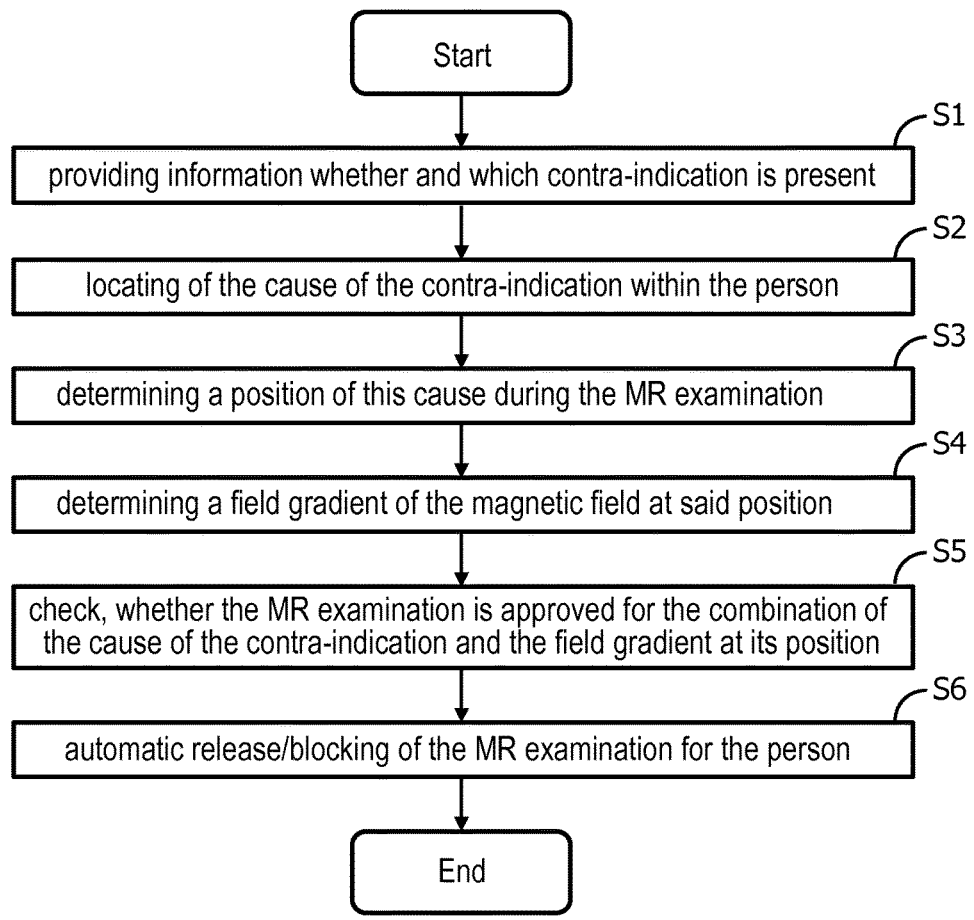
FIG. 2 shows a kind of process flow chart of a process for a semi-automatic detection whether an MR examination of a person is approved with a given MR system according to preferred embodiments of the invention.

FIG. 2 shows a kind of process flow chart of a process for a semi-automatic detection whether an MR examination of a person is approved with the MR system 10.

The process comprises the following steps:

Step 1 (S1): the person 12 to be examined provides information whether and which contra-indication for an MR examination is present. A typical contra-indication is an implant or a pregnancy of the person 12. The operator of the MR system 10 enters the corresponding data of the person and the contra-indication to the user interface 26 of the safety module 28.

Step 2 (S2): the person 12 to be examined provides information about a location of a cause 30 of the contra-indication within his body.

Step 3 (S3): the operator of the MR system 10 determines a position of this cause 30 during the MR examination with respect to the at least one coil 14, 16, 18 and enters the corresponding data to the user interface 26.

Alternatively, in step 3 (S3) the operator of the MR system 10 enters the corresponding data to the user interface 26 and the safety module 28 determines a position of this cause 30 during the MR examination with respect to the at least one coil 14, 16, 18 automatically.

Step 4 (S4) is an automatic determination of at least one characteristic parameter of the magnetic field generated by said coil 14, 16, 18 at said position of the cause 30 during the MR examination. The automatic determination is performed by the safety module 28. In general the spatial gradient field (measured e.g. in Gauss/cm) is the most relevant parameter of the magnetic field.

Step 5 (S5) is an automatic check, whether the MR examination is approved for the combination of the determined cause 30 of the contra-indication and the determined characteristic parameter of the magnetic field at the location of said cause 30. The automatic check is performed by the safety module 28.

Step 6 (S6) is an automatic release of the MR examination of the person 12 in case the MR examination is approved and an automatic blocking of the MR examination of the person 12 in case the MR examination is not approved.

Preferably, the information about the potential contra-indications and the information about the location/position of the cause 30 of the contra-indication is requested by a request routine, which is performed automatically on the user interface 26.

Figure 3:
FIG. 3 shows a first request-mask of a request routine presented by a user interface (UI) for performing the process presented in FIG. 2.
Figure 4:
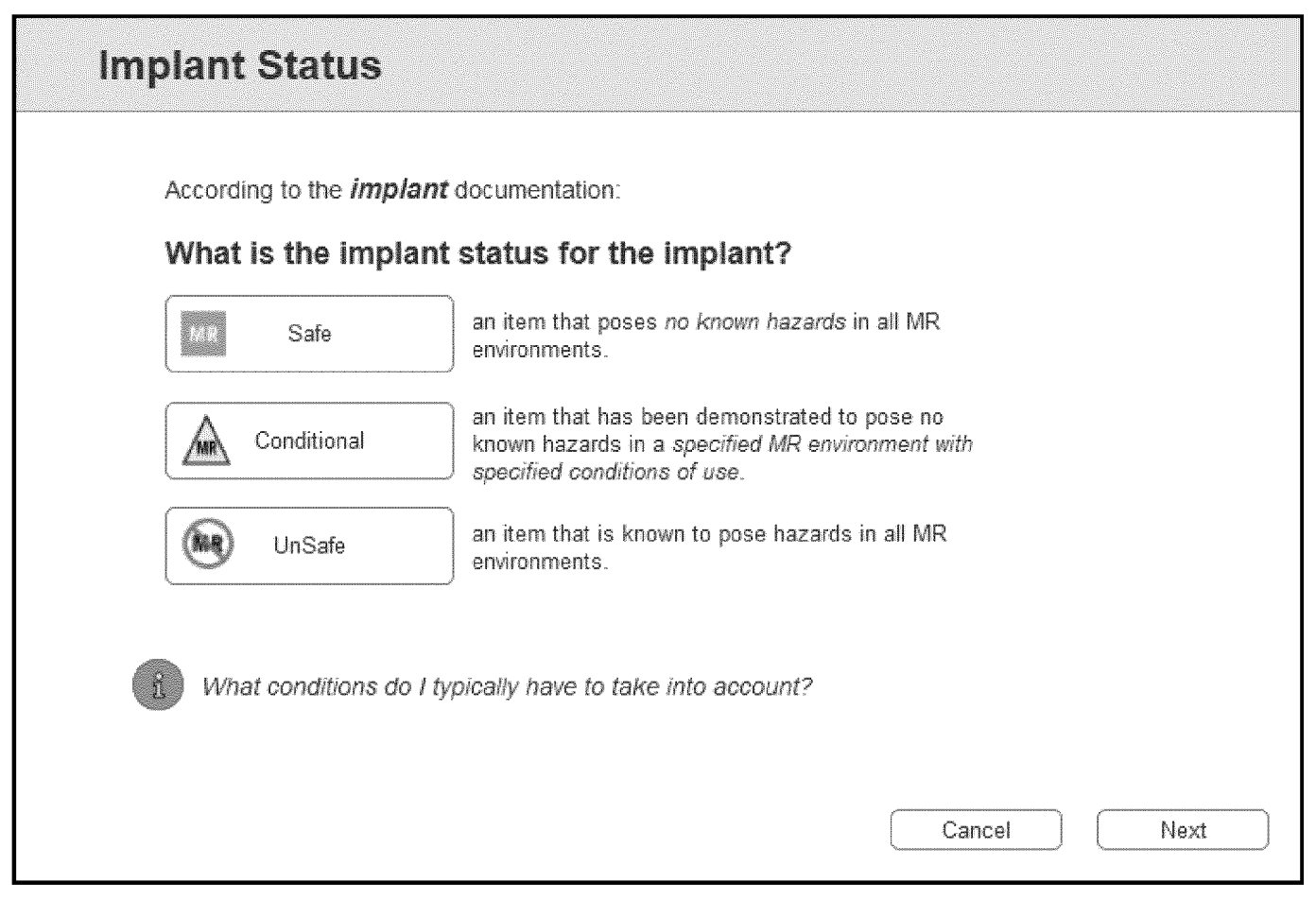
Figure 5:
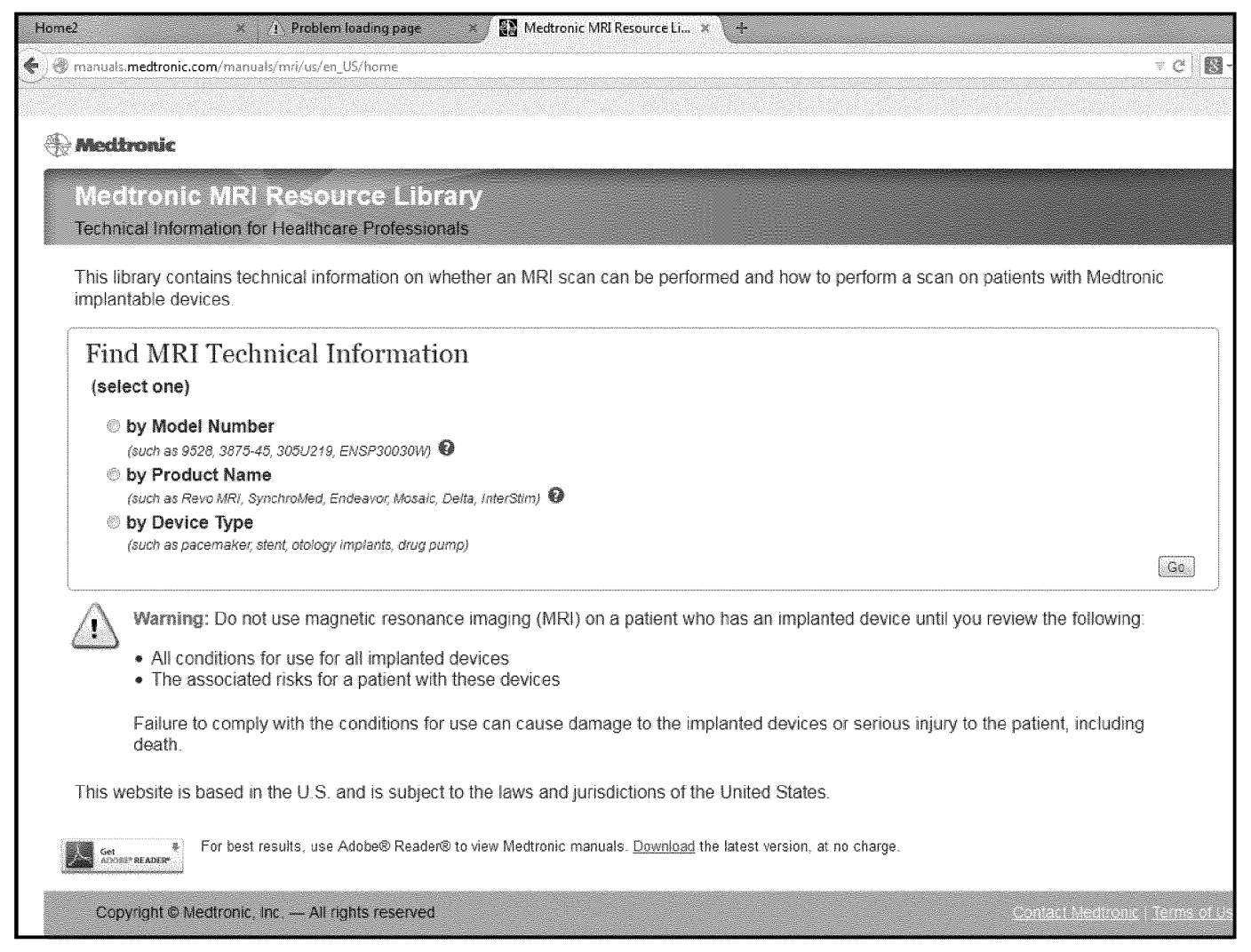

FIGS. 3 to 6 show different request-masks of said request routine. FIG. 3 shows the request-mask of step 1. Personal data and data about the contra-indication for the MR examination are requested. In other words: Patient conditions that require a restriction of the MR scanner output are offered as input fields of the Patient Administration UI 26. FIG. 4 shows an additional request-mask of step 1 requesting a status flag of the implant (status safe/unconditional/unsafe). The input fields for the Implant conditions are aligned to standards like ASTM F2503-8 used by implant manufacturers. FIG. 5 shows the request-mask of a request for a look-up table of possible implants. Resource like implant manufacturer database could be integrated with the UI 26 for quick access to implant information. This could be used as reference, or direct input of MR conditions into the scanner to eliminate operator workflow steps.

Figure 6:
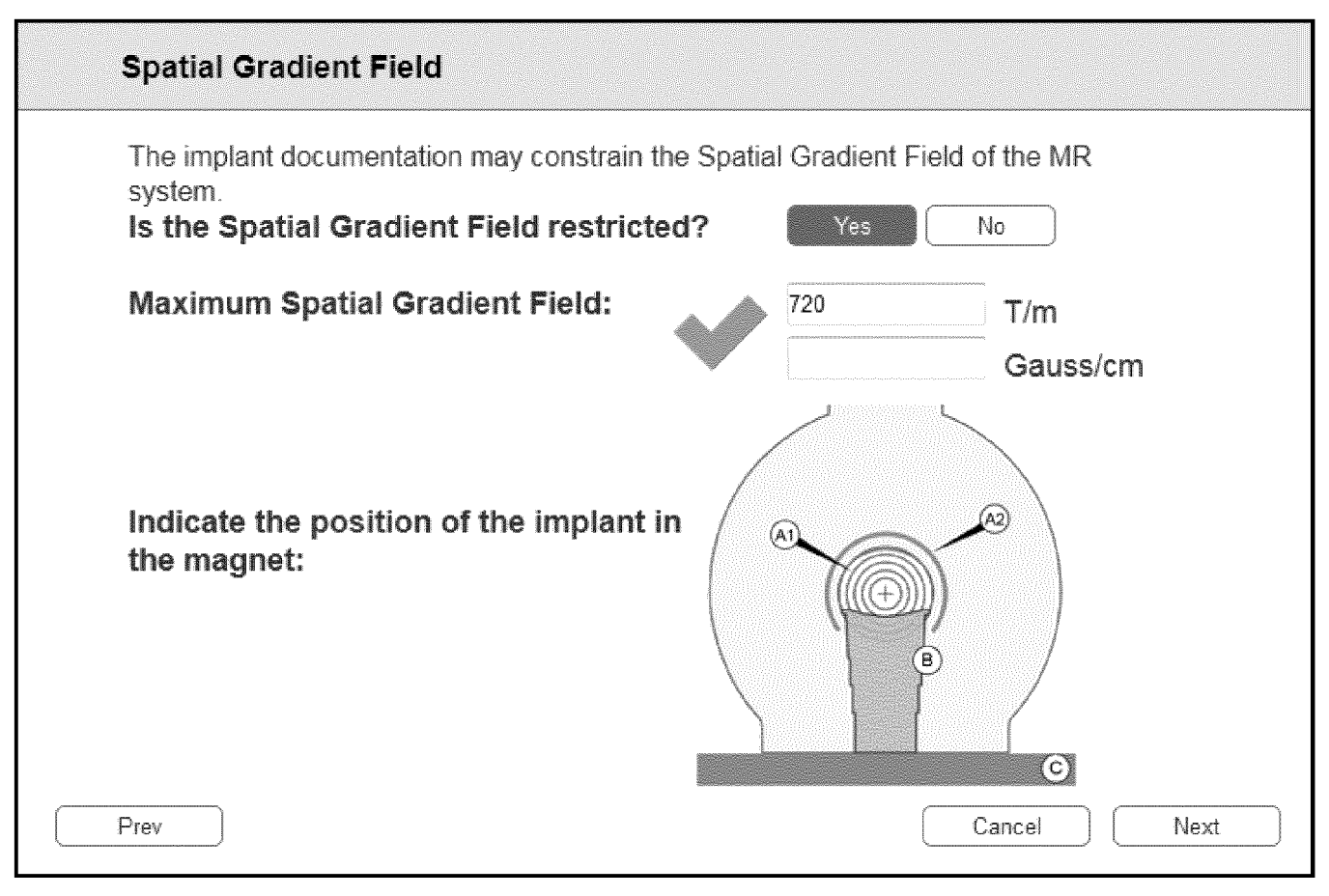

FIG. 6 shows the request-mask of step 3 and 4. The spatial gradient field in relation to the implant position is graphically and interactively visualized. Spatial gradient fields are complex to interpret by MR operators, yet the majority of static implants require evaluation of this MR conditions. Currently this is achieved by the operator having to retrieve this information from the technical documentation and interpret Gradient Plots. The UI 26 offers an interactive method where the operator indicates the implant location by a mouse click and inputs the maximum value as stated in the implant labeling. The Implant UI will indicate to the user of that spatial gradient field condition is met.

Figure 7:
FIG. 7 shows a file system for the corresponding data.

FIG. 7 shows a file system for the corresponding data. An icon indicates which of the suggested ExamCards adhere to the MR restrictions dictated by the Implant conditions.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for an automatic or semi-automatic detection whether a selected magnetic resonance (MR) examination of a person is approved with a predetermined MR system, which MR system includes at least one coil for generating a magnetic field, wherein the method comprises:
  providing information whether and which contra-indication for such a selected MR examination is present for the person;
  providing information about a location of a cause of the contra-indication within the person;
  determining a position of the cause of the contra-indication during the selected MR examination of said person with respect to the at least one coil;
  determining at least one characteristic parameter of the magnetic field generated by said coil at said position of the cause of the contra-indication when the selected MR examination is performed;
  automatically determining the at least one characteristic parameter of the magnetic field at the location of the cause of the contra-indication from a scan protocol for the selected examination; and
  automatically checking whether the selected MR examination is approved for the combination of the determined cause of the contra-indication and the determined characteristic parameter of the magnetic field at the position of said cause of the contra-indication.

2. The method according to claim 1, wherein the information about at least one of:
  the potential contra-indication for the selected MR examination of the person;
  the location of the cause of the contra-indication within the person; and
  the position of the cause of the contra-indication during the MR examination of said person with respect to the at least one coil is/are provided by use of a manual input via a user interface and/or a manual selection from a list presented by said user interface.

3. The method according to claim 2, wherein the user interface requests the information automatically by means of a request routine.

4. The method according to claim 1, further comprising:
automatically releasing the MR examination of the person in case the selected MR examination is approved and automatically blocking of the selected MR examination of the person in case the selected MR examination is not approved.

5. The method according to claim 1, including:
specifying the person's identity before determining the contra-indication.

6. The method according to claim 1, wherein the characteristic parameter of the magnetic field generated by the at least one coil is a field gradient.

7. The method according to claim 1, wherein the cause of the contra-indication is an implant or a pregnancy of the person.

8. A computer program product in a non-transitory computer readable medium for executing the method according to claim 1.

9. The method according to claim 1, wherein:
the information about the location is provided from a radiology information system or input on a user interface; and
the position of the cause of the contra-indication and the characteristic parameter of the generated magnetic field at the position of the cause of the contra-indication are determined from a protocol of the selected MR examination.

10. A safety module for an MR system, which MR system includes at least one coil configured for generating a magnetic field during an MR examination, wherein the safety module has access to the technical characteristics of the predetermined MR system and is configured to:
receive information whether a potential contra-indication for said MR examination is present for this person;
receive a location of a cause of an actual contra-indication within the person;
automatically determine a position of the actual cause of the contra-indication during the MR examination of said person with respect to the at least one coil;
determine at least one characteristic parameter of the magnetic field generated by said at least one coil at said position of the cause of the contra-indication during the MR examination from a protocol for the MR examination; and
automatically check whether the MR examination is approved for the combination of the determined cause of the contra-indication and the determined characteristic parameter of the magnetic field at the position of said cause of the contra-indication.

11. The module according to claim 10, wherein the receipt of information about the location of the cause of the contra-indication is performed by use of a manual input and/or a manual selection from a list presented by a user interface.

12. The module according to claim 11, wherein the information about the potential contra-indications for the MR examination of the person is requested by a request routine, which is performed automatically on the user interface.

13. The module according to claim 10, wherein the module is further configured to:
send a control signal to a control unit of the MR system to automatically release the MR examination of the person when the MR examination is approved and automatically block the MR examination of the person when the MR examination is not approved.

14. The module according to claim 10, wherein the characteristic parameter of the magnetic field generated by the at least one coil includes a characteristic parameter of a magnetic field gradient at the position of the cause of the contra-indication.

15. An MR system for performing the MR examination of a person, the MR system including:
a control unit;
at least one coil for generating a magnetic field in an examination zone; and
the safety module according to claim 10.

16. The MR system according to claim 15, comprising
a gradient system to apply a gradient magnetic field in the examination zone,
a user interface, the safety module being configured to display a gradient strength distribution on the user interface to highlight regions in which the gradient strength exceeds a pre-set safety level.

17. The safety module according to claim 10, wherein the position of the at least one characteristic parameter includes magnetic field strength.

18. A safety system for a magnetic resonance (MR) system that includes coils configured to generate a main magnetic field and magnetic field gradients in an examination zone, the safety system comprising:
a user interface configured to receive information from a user and display information to the user;
a processor configured to:
determine a location in the patient of any implant or an interventional instrument using information received from a radiology information system and the user interface,
access a protocol for a selected MR examination and determine (a) a position of the location of the implant or interventional instrument in the examination zone and (b) a characteristic of the magnetic fields to be applied at the determined position during the selected MR examination,
check whether applying magnetic fields with the determined characteristic of the magnetic fields at the determined position of the implant or interventional instrument exceeds pre-set safety guidelines,
in response to the characteristic of the magnetic fields exceeding the pre-set safety guidelines, at least one of blocking the MR examination and controlling the user interface to display a warning.

19. The safety module according to claim 18, wherein the characteristic of the magnetic fields includes a strength of the gradient magnetic field.

* * * * *